United States Patent
Lincoln et al.

(10) Patent No.: US 11,988,602 B2
(45) Date of Patent: May 21, 2024

(54) SURFACE PLASMON RESONANCE DETECTION SYSTEM

(71) Applicant: Carrier Corporation, Palm Beach Gardens, FL (US)

(72) Inventors: David L. Lincoln, Cromwell, CT (US); Michael J. Birnkrant, Wethersfield, CT (US); Jose-Rodrigo Castillo-Garza, West Hartford, CT (US); Marcin Piech, East Hampton, CT (US); Catherine Thibaud, Cork (IR); Michael J. Giering, Bolton, CT (US); Kishore K. Reddy, Vernon, CT (US); Vivek Venugopalan, South Riding, VA (US)

(73) Assignee: Carrier Corporation, Palm Beach Gardens, FL (US)

( * ) Notice: Subject to any disclaimer, the term of this patent is extended or adjusted under 35 U.S.C. 154(b) by 726 days.

(21) Appl. No.: 17/054,300

(22) PCT Filed: May 10, 2019

(86) PCT No.: PCT/US2019/031684
§ 371 (c)(1),
(2) Date: Nov. 10, 2020

(87) PCT Pub. No.: WO2019/217792
PCT Pub. Date: Nov. 14, 2019

(65) Prior Publication Data
US 2021/0208068 A1 Jul. 8, 2021

Related U.S. Application Data

(60) Provisional application No. 62/670,155, filed on May 11, 2018.

(51) Int. Cl.
*G01N 21/552* (2014.01)
*G01N 27/12* (2006.01)
(Continued)

(52) U.S. Cl.
CPC ......... *G01N 21/553* (2013.01); *G01N 27/125* (2013.01); *G01N 29/036* (2013.01);
(Continued)

(58) Field of Classification Search
CPC .. G01N 21/553; G01N 27/125; G01N 29/036; G01N 33/0034; G01N 2201/1296; G01N 2291/0256
See application file for complete search history.

(56) References Cited

U.S. PATENT DOCUMENTS 4,802,824 A 2/1989 Gastebois et al.
5,275,536 A 1/1994 Stephens et al.
(Continued)

FOREIGN PATENT DOCUMENTS

DE 10054351 A1 * 5/2002 ........... G01N 21/553
DE 10054351 A1 5/2002
(Continued)

OTHER PUBLICATIONS

Gaspera, Enrico Della, et al. "Au Nanoparticles in Nanocrystalline TiO2—NiO Films for SPR-Based, Selective H2S Gas Sensing," Chemistry of Materials (2010, 22 (11), pp. 3407-3417), Publication Date: May 11, 2010, American Chemical Society, Copyright 2010. Web location: http://pubs.acs.org/doi/abs/10.1021/cm100297q.
(Continued)

*Primary Examiner* — Jamil Ahmed
(74) *Attorney, Agent, or Firm* — Carlson, Gaskey & Olds, P.C.

(57) ABSTRACT

An example SPR detection system includes a first prism having a first surface adjacent to a first metal layer exposed to a sample gas, and a second prism having a second surface adjacent to a second metal layer exposed to a reference gas. At least one light source is configured to provide respective beams to the first and second surfaces, where each of the
(Continued)

beams causes SPR of a respective one of the metal layers. At least one photodetector is configured to measure a reflection property of reflections of the respective beams from the metal layers during the SPR. A controller is configured to determine whether a target gas is present in the sample gas based on a known composition of the reference gas and at least one of an electrical property of the first and second metal layers during the SPR and the reflection property of the metal layers.

17 Claims, 8 Drawing Sheets

(51) Int. Cl.
  *G01N 29/036* (2006.01)
  *G01N 33/00* (2006.01)
(52) U.S. Cl.
  CPC . *G01N 33/0034* (2013.01); *G01N 2201/1296* (2013.01); *G01N 2291/0256* (2013.01)

(56) References Cited

U.S. PATENT DOCUMENTS

| | | | |
|---|---|---|---|
| 5,322,798 A | 6/1994 | Sadowski | |
| 7,118,712 B1* | 10/2006 | Manginell | G01N 1/40 96/108 |
| 7,229,253 B2 | 6/2007 | Broderick et al. | |
| 8,057,163 B2 | 11/2011 | Thompson, Jr. et al. | |
| 9,410,909 B2 | 8/2016 | Van Hal et al. | |
| 2006/0197960 A1* | 9/2006 | Bazylenko | G01N 21/253 356/491 |
| 2006/0213697 A1 | 9/2006 | Sutherland | |
| 2007/0048142 A1 | 3/2007 | Dambrine et al. | |
| 2007/0148702 A1 | 6/2007 | Nakamura et al. | |
| 2008/0035180 A1 | 2/2008 | Mutharasan | |
| 2009/0016890 A1 | 1/2009 | Douguet et al. | |
| 2009/0061946 A1 | 3/2009 | George | |
| 2010/0008782 A1 | 1/2010 | Danescu et al. | |
| 2011/0022665 A1 | 1/2011 | Pinto et al. | |
| 2011/0022666 A1 | 1/2011 | Pinto | |
| 2011/0211965 A1 | 9/2011 | Deal et al. | |
| 2011/0298841 A1 | 12/2011 | Fujimori | |
| 2012/0131197 A1 | 5/2012 | Prentice et al. | |
| 2013/0110327 A1 | 5/2013 | Fernandez | |
| 2013/0204456 A1 | 8/2013 | Tippelhofer et al. | |
| 2013/0302173 A1 | 11/2013 | Booze et al. | |
| 2014/0154073 A1 | 6/2014 | Cairo et al. | |
| 2015/0020577 A1 | 1/2015 | Luebke et al. | |
| 2016/0187280 A1* | 6/2016 | Potyralio | G01N 31/10 324/675 |
| 2016/0334327 A1 | 11/2016 | Potyrailo et al. | |
| 2017/0344879 A1 | 11/2017 | Merhav et al. | |
| 2020/0388028 A1* | 12/2020 | Agus | G16H 50/20 |

FOREIGN PATENT DOCUMENTS

| | | | |
|---|---|---|---|
| EP | 2108941 A2 | 10/2009 | |
| EP | 3040716 A1 | 7/2016 | |
| JP | H09257699 A * | 10/1997 | ........... G01N 21/533 |
| JP | H09257699 A | 10/1997 | |
| JP | 2007263736 A * | 10/2007 | ........... G01N 21/552 |
| JP | 2007263736 A | 10/2007 | |

OTHER PUBLICATIONS

Kaushik, Ajeet, et al. "Nanostructured Gas Sensors for Health Care: An Overview," Journal of Personalized NanoMedicine, Published online: Jul. 27, 2015. Copyright: 2015 OLOGY Group. http://jpnmjournal.org/articles/Nanostructured-Gas-Sensors-for-Health-Care-An-Overview.pdf.

Nooke, Alida, "Gas Detection by Means of Surface Plasmon Resonance enhanced Ellipsometry," Dissertation. Publication Date: Mar. 16, 2012. Berlin, Germany. https://d-nb.info/1021976253/34.

Wadell, Carl, et al. "Nanoplasmonic Hydrogen Sensing," Department of Applied Physics, Chalmers University of Technology, 412 96 Goeteborg, Sweden, 2014. http://publications.lib.chalmers.se/records/fulltext/209154/local_209154.pdf.

Gaspera, Enrico Della, et al. "Sol-Gel Thin Films for Plasmonic Gas Sensors," Sensors, ISSN 1424-8220, www.mdpi.com/journal/sensors, Published: Jul. 13, 2015.

Mishra, Akhilesh Kumar, et al. "Gas Sensing in Kretschmann Configuration Utilizing bi-Metallic Layer of Rhodium-Silver in Visible Region," ScienceDirect, Sensors and Actuators B: Chemical, Dept. of Electrical Engineering, Technion-Israel Institute of Technology, Haifa 32000, Israel. 2016 Downloaded from: https://www.sciencedirect.com/science/article/pii/S0925400516310760.

Llobet, Eduard, et al. "Nanomaterials for the Selective Detection of Hydrogen Sulfide in Air," Sensors, MDPI, Published Feb. 17, 2017, Basel, Switzerland. Downloaded from: https://www.ncbi.nlm.gov/pmc/articles/PMC5336037/.

Usha, Sruthi P., et al. "Fabrication and Characterization of a SPR Based Fiber Optic Sensor for the Detection of Chlorine Gas Using Silver and Zinc Oxide," Materials, ISSN 1996-1944, Published: Apr. 28, 2015, www.mdpi.com/journal/materials, 2015.

Pang, H., et al. "On-Chip Surface Plasmon Resonance Sensor," Oct. 2008. PubMed.gov, Downloaded from: https://www.ncbi.nlm.nih.gov/pubmed/19198372.

Kreno, Lauren E., et al. "Metal-Organic Framework Thin Film for Enhanced Localized Surface Plasmon Resonnce Gas Sensing," Analytical Chemistry, 2010, 82 (19), pp. 8042-8046. Publication date: Sep. 14, 2010. Copyright 2010, American Chemical Society. Downloaded from: https://pubs.acs.org/doi/abs/10.1021/ac102127p.

Nore, Per Wessel. "Pollution Detection in a Low-Cost Electronic Nose, a Machine Learning Approach," Master's Thesis Autumn 2016, University of Oslo, Department of Informatics.

Kim, Eun Gyeong, et al. "Pattern Recognition for Selective Odor Detection with Gas Sensor Arrays," Sensors 2012, ISSN 1424-8220, www.mdpi.com/journal/sensors, Published: Nov. 23, 2012.

International Search Report and Written Opinion for International Patent Application No. PCT/US2019/031684 dated Oct. 1, 2019.

* cited by examiner

SURFACE PLASMON RESONANCE DETECTION SYSTEM

CROSS-REFERENCE TO RELATED APPLICATIONS

This is a national stage application, filed under 35 U.S.C. § 371, of International Patent Application No. PCT/US2019/031684, which was filed on May 10, 2019, which claims the benefit of U.S. Provisional Patent Application No. 62/670,155, which was filed on May 11, 2018, each of which is incorporated by reference herein in its entirety.

BACKGROUND

This application relates to a chemical detector, and more particularly to a surface plasmon resonance detection system.

Detection systems can be used to identify smoke or chemicals for early warning of a threat event, for security purposes, or the like. As examples, systems may be designed to identify trace amounts of smoke particles in a building as an early warning of a fire, trace amounts of a target chemical as an early warning of toxicity of an environment, or minute amounts of airborne substances on humans, luggage, packages, or other objects as a security measure.

One type of chemical detector is a surface plasmon resonance (SPR) detector. Surface plasmon resonance (SPR) is an optical effect that can be utilized to measure the binding or "adsorption" of molecules onto a metal surface. In one SPR configuration, a beam of light is directed through a glass prism to a metal-coated face of the glass prism. The beam of light is reflected from the metal-coated face at an angle that excites electrons in the metal layer, causing them to resonate. This resonance is known as a "surface plasmon resonance." This resonance is modified when a compound is adsorbed onto the metal layer. One drawback of some SPR detectors is their propensity to give false positive results.

SUMMARY

A SPR detection system according to an example of the present disclosure includes a first prism having a first surface adjacent to a first metal layer that is exposed to a sample gas, and a second prism having a second surface adjacent to a second metal layer that is exposed to a reference gas. At least one light source is configured to provide respective beams to the first and second surfaces, where each of the beams causes SPR of a respective one of the metal layers. At least one photodetector is configured to measure a reflection property of reflections of the respective beams from the metal layers during the SPR. A controller is configured to determine whether a target gas is present in the sample gas based on a known composition of the reference gas and at least one of an electrical property of the first and second metal layers during the SPR and the reflection property of the first and second metal layers.

In a further embodiment of any of the foregoing embodiments, the controller is configured to determine that the target gas is present in the sample gas based on at least one of a change in the electrical property of the first metal layer and a change in the reflected beam from the first surface indicating adsorption of the target gas to the first metal layer.

In a further embodiment of any of the foregoing embodiments, the SPR detection system includes a cantilevered piezoelectric beam having a first end that is secured to a support, and second, free end that is opposite the first end and has a metal coating. A vibration device is configured to vibrate the cantilevered piezoelectric beam at its resonant frequency. The controller is configured to further base its determination of whether the sample gas includes the target gas on whether a change in the resonant frequency indicates adsorption of the target gas to the metal coating.

In a further embodiment of any of the foregoing embodiments, the light source includes a beam splitter configured to split a beam from the light source into a first beam directed to the first prism and a second beam directed to the second prism.

In a further embodiment of any of the foregoing embodiments, each metal layer includes gold.

In a further embodiment of any of the foregoing embodiments, the target gas is hydrogen sulfide.

In a further embodiment of any of the foregoing embodiments, the reference gas is inert.

In a further embodiment of any of the foregoing embodiments, each metal layer includes a serpentine electrical trace deposited onto its surface adjacent to its respective prism, and the electrical property of the metal layer is measured across the serpentine electrical trace.

In a further embodiment of any of the foregoing embodiments, the electrical property of each metal layer includes a resistance of the metal layer, an amplitude of an electrical signal provided across the metal layer, or a frequency of an electrical signal provided across the metal layer.

In a further embodiment of any of the foregoing embodiments, the SPR detection system includes at least one electrical detector configured to determine the electrical property of the first and second metal layers during the SPR.

In a further embodiment of any of the foregoing embodiments, the electrical detector includes a first bridge circuit configured to measure a resistance of the first metal layer during the SPR of the first metal layer, and a second bridge circuit configured to measure a resistance of the second metal layer during the SPR of the second metal layer.

In a further embodiment of any of the foregoing embodiments, each bridge circuit includes first, second, third, and fourth nodes. The first node is coupled to each of a first portion of its associated metal layer, a first resistor, and a current measurement device. The second node is coupled to each of a second portion of the associated metal layer, a second resistor, and a power source. The third node is coupled to each of the first resistor, the power source, and a third resistor. The fourth node is coupled to each of the second resistor, the third resistor, and the current measurement device.

In a further embodiment of any of the foregoing embodiments, the SPR detection system includes a pair of spaced apart walls that face each other, with at least one of the first prism and the second prism disposed between the pair of spaced apart walls. A plurality of fins extend between the pair of spaced apart walls and are disposed around the at least one prism. The walls and plurality of fins define a gas chamber around the at least one prism, and the plurality of fins are spaced apart from each other to define channels for gas to enter and exit the gas chamber.

In a further embodiment of any of the foregoing embodiments, the plurality of fins are cascaded such that a portion of each fin extends outside of the chamber.

In a further embodiment of any of the foregoing embodiments, the first and second prisms are disposed between the same pair of spaced apart walls.

In a further embodiment of any of the foregoing embodiments, the SPR detection system includes at least one heater configured to induce desorption of analytes from the first and second metal layers by heating the first and second metal layers.

A SPR detection system according to an example of the present disclosure includes a light propagation structure including a surface and a plurality of waveguides. A plurality of metal layers include different metal oxide frameworks (MOFs) having differing porosities and different binding affinities for a plurality of different target gases. The plurality of metal layers are arranged in an array on the surface and are exposed to a sample gas. A plurality of light sources are configured to provide respective beams through the plurality of waveguides to the surface that cause SPR of each metal layer. An array of photodetectors is included, each photodetector associated with one of the metal layers, and configured to measure a reflection property of a reflection of one of the beams from an interface of the surface and its associated metal layer. A controller is configured to determine an electrical property of the plurality of metal layers during the SPR, and determine whether any of the target gases are present in the sample gas based on at least one of the electrical properties and the reflection properties of the metal layers.

In a further embodiment of any of the foregoing embodiments, each metal layer is adjacent to a companion metal layer that is coated to prevent adsorption of analytes to the companion metal layer. The controller is configured to compare at least one of the electrical property and the reflection property from each of the plurality of metal layers to at least one of an electrical property and a reflection property from its corresponding companion metal layer as part of the determination of whether any of the target gases are present in the sample gas.

In a further embodiment of any of the foregoing embodiments, each metal layer has the same MOF composition as its companion metal layer.

In a further embodiment of any of the foregoing embodiments, the plurality of metal layers and companion metal layers are coplanar.

In a further embodiment of any of the foregoing embodiments, the plurality of light sources include a respective light emitter for each row of the array of metal layers, and each waveguide is configured to guide a beam from a given one of the light emitters towards the metal layers of its associated row at predefined angles.

In a further embodiment of any of the foregoing embodiments, a plurality of heaters are disposed adjacent to individual ones of the metal layers, each heater configured to induce desorption of analytes from its adjacent metal layer by heating its adjacent metal layer.

A chemical detection system according to an example of the present disclosure includes a plurality of detectors arranged for collecting data from a gas sample. Each detector includes a respective metal layer. Various ones of the metal layers have differing binding affinities for a plurality of target gases. The plurality of detectors are configured to use at least one of SPR and photoacoustic detection techniques to collect data about the gas sample. A processor is configured to perform a machine learning-based analysis to determine whether any of the target gases are present in the gas sample based on the data collected by the plurality of detectors from the gas sample.

In a further embodiment of any of the foregoing embodiments, to perform the machine learning-based analysis, the processor is configured to: apply at least one machine learning technique to a set of historical training data to produce a nodal set that represents at least one of spatial and temporal correlations in the set of historical training data, the training data gathered by the plurality of detectors when exposed to a plurality of different training gases having known compositions; and utilize the nodal set to determine whether any of the target gases are present in the gas sample based on the data collected by the plurality of detectors from the gas sample.

In a further embodiment of any of the foregoing embodiments, the nodal set includes a neural network comprising at least one of a recurrent neural network and a convolutional neural network.

In a further embodiment of any of the foregoing embodiments, the data collected by the plurality of detectors from the gas sample includes a change in resistance across a plurality of the metal layers when the plurality of metal layers are resonating due to SPR and are exposed to the gas sample.

In a further embodiment of any of the foregoing embodiments, the data collected by the plurality of detectors from the gas sample includes a change in amplitude, frequency, or both, of respective electrical signals across respective ones of the metal layers when the respective ones of the metal layers are resonating due to SPR and are exposed to the gas sample.

In a further embodiment of any of the foregoing embodiments, the data collected by the plurality of detectors from the gas sample includes changes in reflection properties of beams reflected from the metal layers are resonating due to SPR and are exposed to the gas sample.

In a further embodiment of any of the foregoing embodiments, the data collected by the plurality of detectors from the gas sample includes desorption data indicative of a time needed for analytes from the gas sample to desorb from various ones of the metal layers.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

DETAILED DESCRIPTION

The embodiments discussed herein disclose a number techniques that improve the sensitivity and reliability of SPR detectors, and also provide for improvements in analyzing of data derived from SPR detectors in general. These improvements mitigate the false positive results common with prior art SPR detectors.

Figure 1:
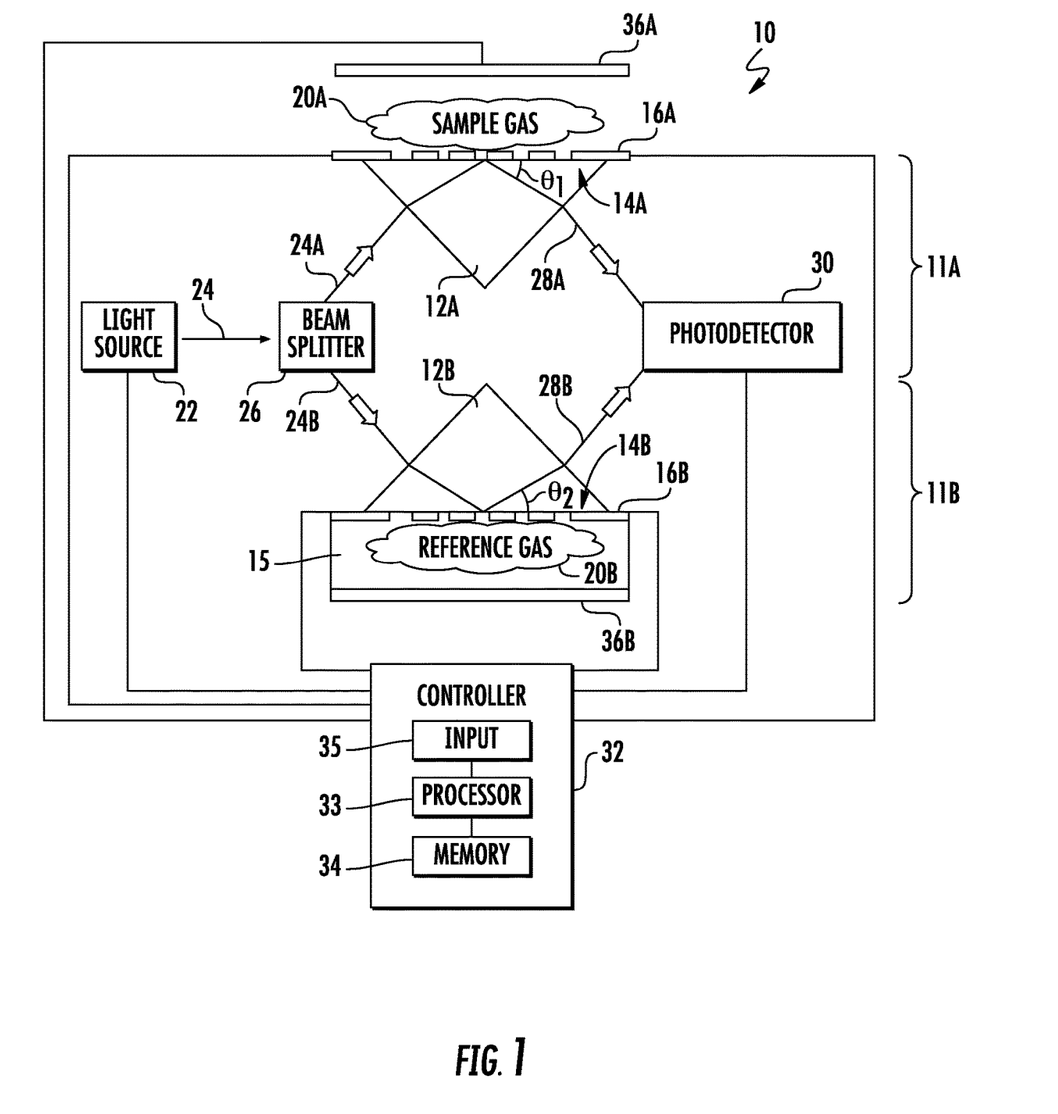
FIG. 1 is a schematic view of an example SPR detection system.

FIG. 1 is a schematic view of an example SPR system 10 that includes two SPR detectors 11A-B. The two SPR detectors 11A-B are used in a differential configuration, with sensor 11B acting as a reference, for improved sensitivity and reliability.

Each SPR detector 11A-B includes a respective prism 12A-B. The prisms 12 can be composed of glass, or a material such as plastic or acrylic having a similar refractive index to that of glass. Glass typically has a refractive index of about 1.5. In one example, the prism 12 has a refractive index of approximately 1.5-2. Each prism 12A-B comprises a respective surface 14A-B that is adjacent to a respective metal layer 16A-B. In one example, the metal layers 16A-B are formed on the respective surfaces 14A-B. In one example, the sensors 11A-B are identical except for the gas that they are exposed to.

The first metal layer 16A is exposed to a sample gas 20A, and the second metal layer 16B is exposed to a reference gas 20B that is in an enclosure 15, has a known composition (e.g., an inert gas such as helium, argon, nitrogen, etc.), and generates a known SPR response. The SPR system 10 is configured to determine whether a sample gas 20A includes a target gas. The target gas can be a contaminant, such as hydrogen sulfide ($H_2S$) gas, for example. However, other target gases could be used that are not necessarily contaminants. In one example the target gas is a byproduct of combustion such as $NO_2$, $NO$, $SO_2$, $SO_3$, methane, $CO_2$, $H_2O$, etc. In one example, the metal layers 16 include gold or silver. Gold is useful for detection of $H_2S$ gas because gold is highly reactive to $H_2S$ gas and mostly inert to other gases.

A light source 22, such as a laser diode, is configured to provide a beam 24 of light to a beam splitter 26 that splits the beam 24 into a first beam 24A and a second beam 24B. The first beam 24A is directed to surface 14A at an interface of the surface 14A and the first metal layer 16A, and reflects back to photodetector 30 as reflection 28A. The second beam 24B is directed to surface 14B at an interface of the surface 14B and the second metal layer 16B, and reflects back to photodetector 30 as reflection 28B. In one example, the photodetector 30 includes at least one photodiode.

A portion of the beam 24A is reflected back at a first angle of minimum reflected intensity $\theta_1$, and a portion of the beam 24B is similarly reflected back at a second angle of minimum reflected intensity $\theta_2$. The beams 24A-B cause electrons in the metal layers 16A-B to resonate. The resonating electrons are known as "surface plasmons" and their resonance is known as "surface plasmon resonance" or SPR. If analyte particles in the gases 20 bind to metal layer 16A, the angle of minimum reflected intensity $\theta$ changes, which is detected by photodetector 30. These changes are indicative of information about the gases 20, such as binding affinity, binding concentration, adsorption time, desorption time, etc.

Adsorption of the target gas by the metal layer 16A modifies the optical and electrical properties of the metal layer 16A, resulting in variation of its surface plasmon resonance and its electrical resistance. For example, the resistance of the metal layer 16A is expected to increase during adsorption of the target gas.

A controller 32 is operatively connected to the light source 22, photodetector 30, and metal layers 16A-B. The controller 32 is configured to pulse the light source 22 to provide the beams 24A-B and operate the photodetector 30 to read the reflections 28A-B based on a timing of the pulses. The controller 32 includes a processor 33, such as a microprocessor, microcontroller, or application specific integrated circuit (ASIC) that is programmed to implement the various techniques discussed herein. The controller 32 includes memory 34 that stores program instructions for the processor 33. The controller 32 also includes an input interface 35 for interacting with the metal layers 16, light source 22, and photodetector 30.

The controller 32 is also operable to take electrical measurements from the metal layers 16A-B while the beams 24 cause SPR on the metal layers 16A-B. The electrical measurements can include resistance, for example, which can change during SPR. As used herein, "during SPR" of a metal layer 16 means when electrons in the metal layer 16 are resonating due to surface plasmon resonance. In one example, the electrical measurements include a change in frequency and/or amplitude of a signal that is provided through the metal layers 16 during the SPR (e.g., from an AC power source, or a DC power source performing pulse width modulation "PWM").

Since the metal layers 16 are thin, the surface area to volume ratio is large. A surface gas attaching to the surface of one of the metal layers 16 will change its electrical resistivity. Electrical resistivity is the low frequency analog of electrical permittivity that gives rise to the surface plasmon resonance.

By probing at low and high frequencies, one can obtain different information about the interaction of the surface of the metal layers 16 with the environment. As an example, at high frequency the SPR probes the attachment of a chemical to the surface. However, a similar change in reflectivity could occur from delamination of the metal layer 16. Measuring electrical resistivity enables validation that the SPR measurement is from surface binding of a sample gas and not a physical change to the metal layer 16.

The controller 32 is configured to determine whether the target gas is present or absent in the sample gas 20A based on one or more electrical properties of the metal layers 16 and based on the reflected beams 28A-B.

The controller 32 is also operable to control heaters 36A-B that are arranged to heat the metal layers 16A-B and induce desorption of analytes from the first and second metal layers 16A-B for a subsequent testing cycle.

The SPR system 10 provides for fail-safe detecting of trace levels of a target gas (e.g., $H_2S$ in concentrations from <1 to 100 ppm). The SPR system 10 detects a target gas by simultaneously monitoring surface plasmon resonance and electrical resistance. Adsorption of the target gas by the metal layer 16 modifies its optical and electrical properties, resulting in the variation of its SPR and its electrical resistance. Both detection mechanisms (i.e., detecting changes in electrical properties and optical properties) allow the SPR system 10 to be fail-safe. If one detection mechanism fails (e.g., no detected change in electrical properties), the other is able to continue monitoring for target gas adsorption without interruption (e.g., continue monitoring optical properties of reflected beam 28). The correlation and calibration of these two detection mechanisms, in conjunction with use of the sensor 11B as a reference sensor, provides a fail-safe device with minimal cross-sensitivity that outperforms current point detectors used in extreme environment (e.g., desert-like environments that are very hot and dry).

Each metal layer 16 has physical properties that enable it to produce a surface plasmon. Permittivity and electron mobility are two key parameters for establishing a surface plasmon at a particular frequency of light. In the case of purely metallic materials periodic table group 11 or 1B elements have the physical properties that enable a surface plasmon. In addition, periodic table group 10, 12, and 14 elements can also support plasmon resonances. The oxides of periodic table group 4-7 elements can produce plasmon resonances at higher frequencies. The selection of the metal layer supports the establishment of the wavelength required to excite the surface plasmon resonance.

Figure 2:
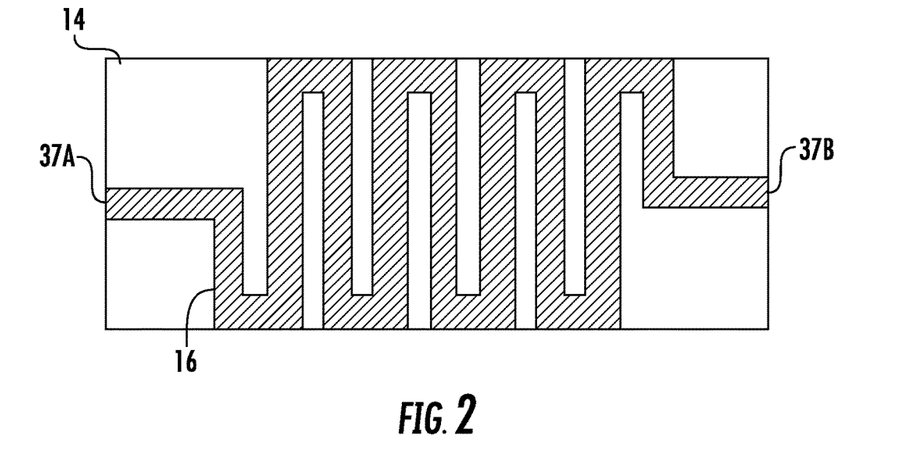
FIG. 2 schematically illustrates an example metal layer that can be deposited onto a surface of a prism in the SPR detection system of FIG. 1.

FIG. 2 schematically illustrates an example metal layer 16 that is deposited onto a surface 14. In one example the depositing is achieved through anodic bonding of the metal layer 16 to the glass surface 14. As shown in FIG. 2, the metal layer 16 provides a trace that follows a serpentine path along the surface 14 and includes ends 37A, 37B operatively connected to controller 32 for measuring electrical properties of the trace (e.g., resistance, amplitude, frequency, etc.), for example, as described below with regards to FIG. 3.

Figure 3:
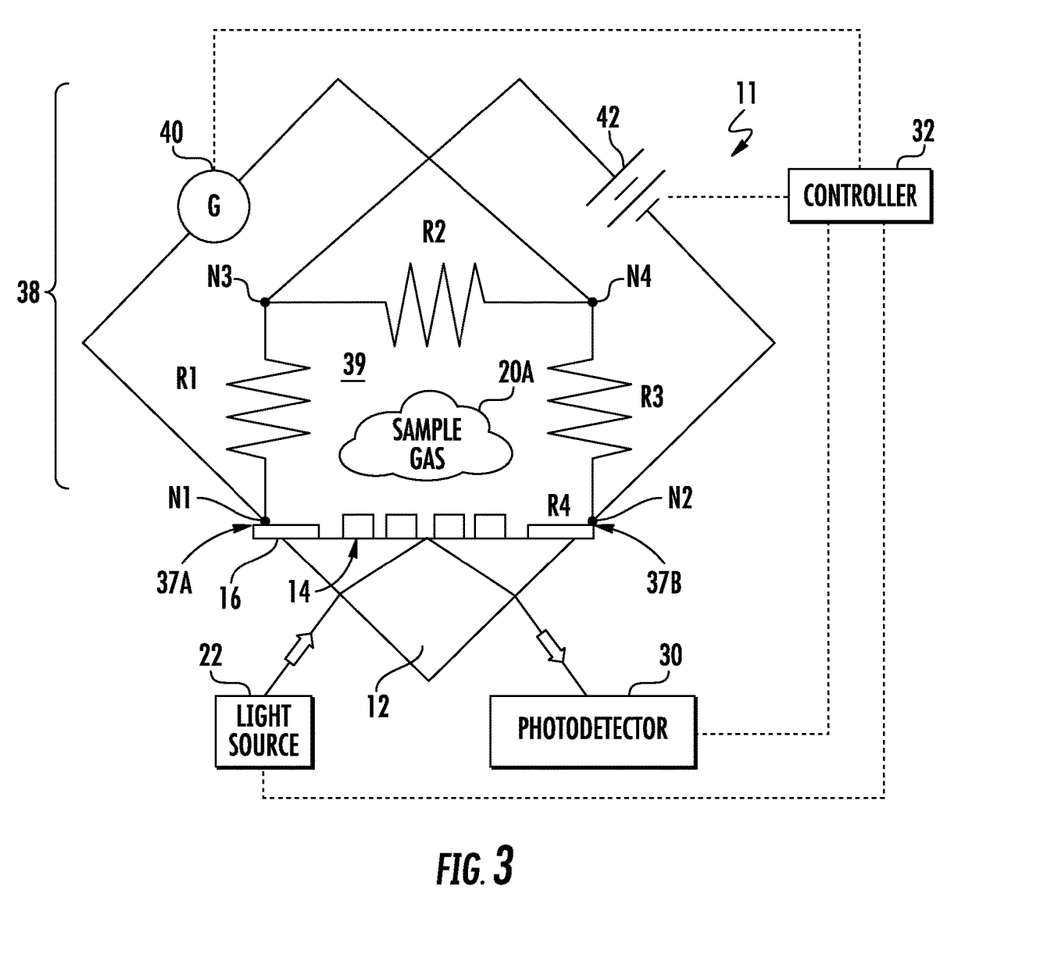
FIG. 3 schematically illustrates an example SPR detector that utilizes an exemplary bridge circuit.

FIG. 3 schematically illustrates an example SPR detector 11 in which the controller 32 utilizes a bridge circuit 38 to measure one or more electrical properties, such as resistance, of the metal layer 16 when exposed to the sample gas 20A in a gas detection area 39. In the non-limiting example of FIG. 3, the bridge circuit 38 utilizes a Wheatstone configuration including nodes N1-N4. Node N1 is coupled to end 37A of metal layer 16, resistor R1, and a galvanometer 40 which measures an electrical current across the metal layer 16. Node N2 is coupled to opposing end 37B of the metal layer 16, resistor R3, and a power source 42. Node N3 is coupled to resistor R1, the power source 42, and a resistor R2. Node N4 is coupled to resistor R2, resistor R3, and the galvanometer 40. In one example the resistors R1, R2, R3 have the same or substantially the same resistance values (e.g., within 1-5% of each other). The more precise the resistor values R1, R2, R3, the more precise the measurements of the bridge circuit 38 will be.

Use of the bridge circuit 38 provides for good electrical property measurement sensitivity, and provides for overall more accurate measurements than would be obtainable without the bridge circuit 38.

Although a single bridge circuit 38 is depicted in FIG. 3, it is understood that separate bridge circuits 38 could be used for the first SPR detector 11A and second SPR detector 11B, respectively.

Figure 4A:
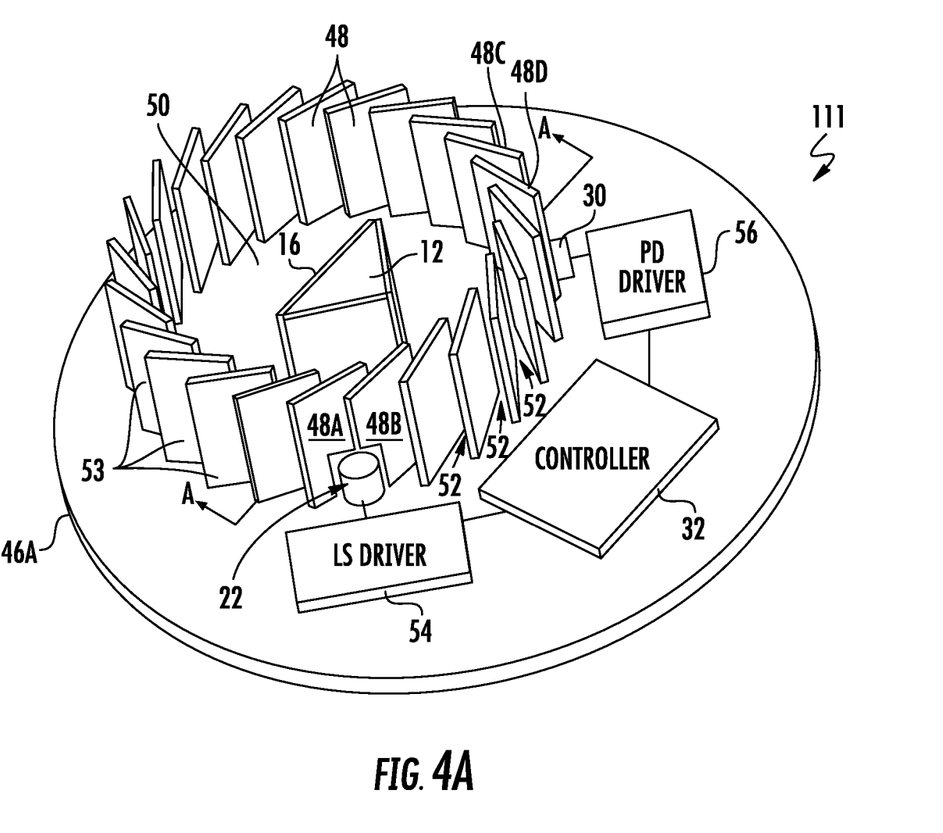
FIG. 4A illustrates an example SPR detector arranged on a platform.

FIG. 4A illustrates an example SPR detector 111 arranged on a platform 46A. In this disclosure, like reference numerals designate like elements where appropriate and reference numerals with the addition of one-hundred or multiples thereof designate modified elements that are understood to incorporate the same features and benefits of the corresponding elements.

A plurality of cascading fins 48 extend upwards from the platform 46A and are circumferentially disposed around the prism 12 and the metal layer 16 adjacent to the prism 12. The fins 48 create a labyrinth which allows ambient air to flow into a gas chamber 50 around the prism 12 which acts as a sensing volume, while blocking and/or reducing an amount of ambient light that enters the gas chamber 50. The fins 48 circumferentially overlap each other such that adjacent pairs of the fins 48 define channels 52 for gas to enter and exit the chamber 50. The fins 48 are cascaded such that a portion 53 of each fin 48 resides outside of the chamber 50.

Figure 4B:
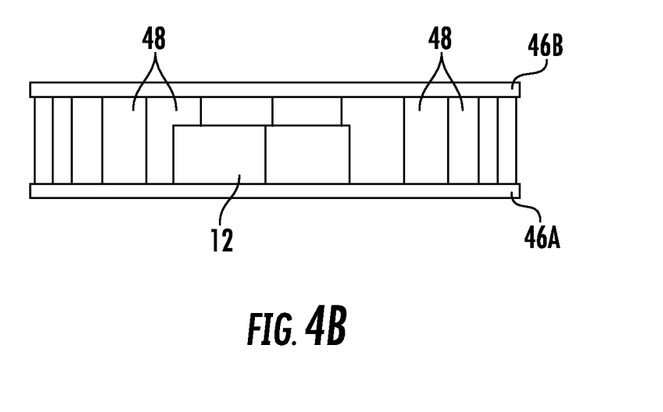
FIG. 4B is taken along line A-A of FIG. 4A.

FIG. 4B is taken along line A-A of FIG. 4A and includes an additional platform 46B. As shown in FIG. 4B, the fins 48 extend between the first platform 46A and the additional second platform 46B. The platforms 46A-B are spaced apart from each other and face each other, and along with the fins 48 define the gas chamber 50. In one example, the platforms 46 act as barriers to minimize an amount of light and dust that enters the gas chamber 50. In the example, the fins 48 are perpendicular to the platforms 46A-B.

Referring again to FIG. 4A, the controller 32 is operatively connected to a light source driver 54 that operates the light source 22 (e.g., a light-emitting diode "LED" or laser diode), and a photodetector driver 56 which operates the photodetector 30 (e.g., a photodiode, avalanche photodiode (APD), multi-pixel photon counter (MPPC), etc.). The fins 48A-B adjacent to light source 22 are notched to avoid obstructing a light beam from the light source 22 to the prism 12, and the fins 48C-D adjacent to photodetector 30 are also notched to avoid obstructing the beam reflected from the prism 12. Although not shown in FIG. 4A, the controller 32 is also operatively connected to the metal layer 16 (e.g., using the bridge circuit of FIG. 3) to measure one or more electrical properties of the SPR detector 111.

In one example, the SPR detectors 11A-B are disposed between the same pair of spaced apart platforms 46A-B, with each SPR detector 111 having its own cascading array of fins 48.

Figure 4C:
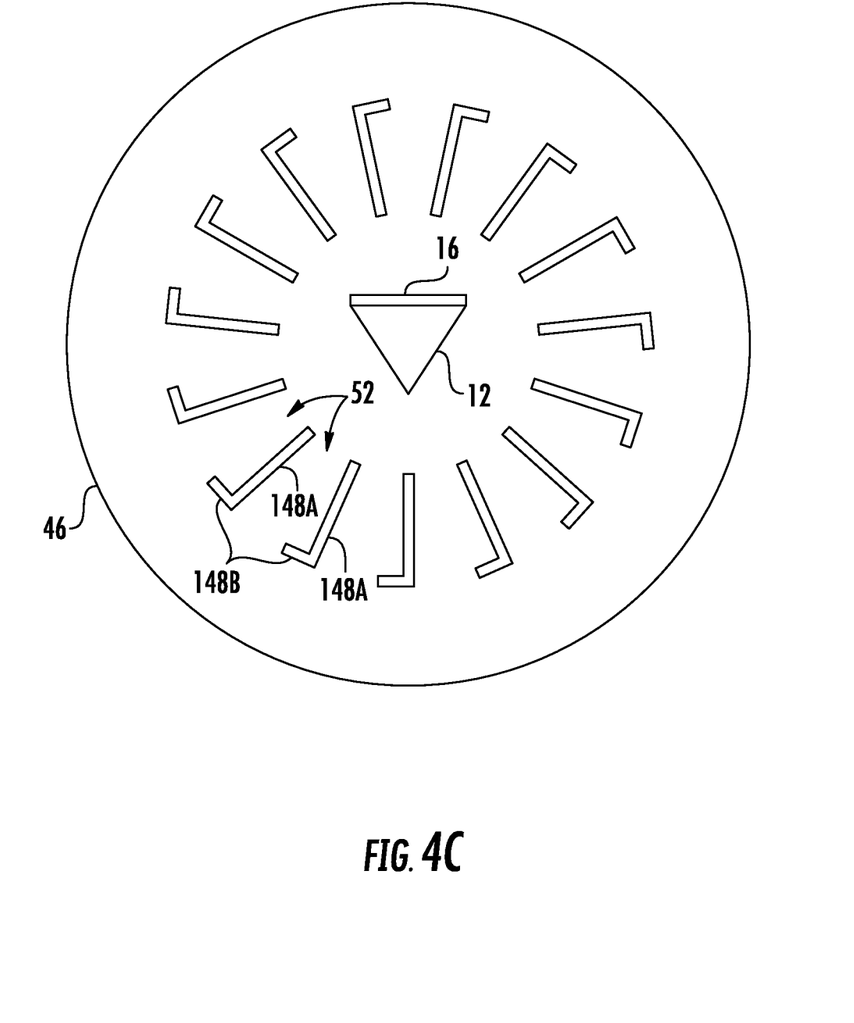
FIG. 4C illustrates another example SPR detector arranged on a platform.

Although a particular fin design is shown in FIG. 4A, it is understood that other configurations could be used, such as the example arrangement of FIG. 4C, in which each fin 148 includes two connected fin portions 148A-B that are angled with respect to each other, and reside in separate planes, with portion 148B partially obstructing an adjacent channel 52. In the example of FIG. 4C, the prism 12 and its adjacent metal layer 16 are still situated on the platform 46, and still include a plurality of cascading fins 148 that extend upwards from the platform 46A and are circumferentially disposed around the prism 12 and the metal layer 16.

Figure 5:
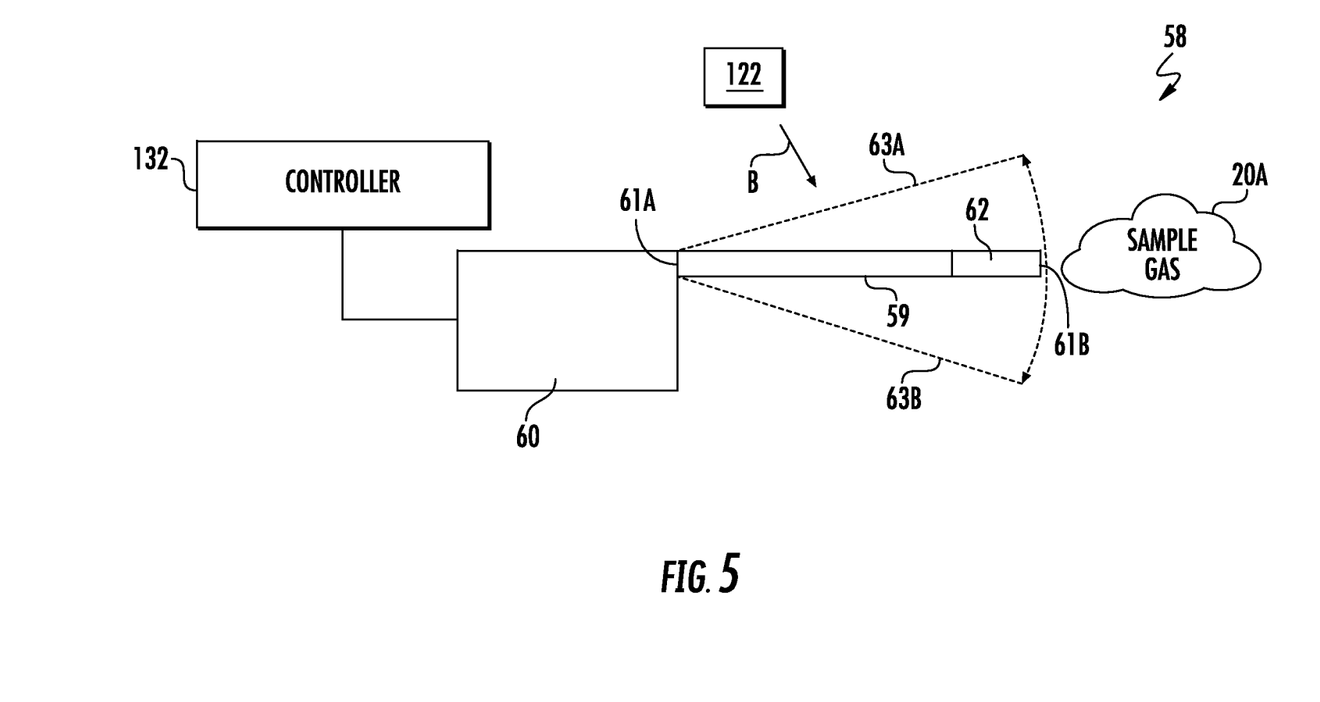
FIG. 5 schematically illustrates an example cantilevered detector.

FIG. 5 schematically illustrates an example cantilevered detector 58 comprising a cantilevered piezoelectric beam 59 that extends from a drive/detection device 60. In particular, a first end 61A of the piezoelectric beam 59 is secured to the drive/detection device 60, and an opposite second end 61B of the piezoelectric beam 59 is a free end that has a metallic coating 62, such as a gold or silver coating. The drive/detection device 60 operates in a drive mode to provide an AC signal having a frequency that causes the piezoelectric beam 59 to vibrate at its resonant frequency. In one example, the signal is provided at a resonant frequency of the piezoelectric beam 59. While the piezoelectric beam 59 is vibrating, the drive/detection device 60 stops providing the AC signal and operates in a detection mode in which the drive/detection device 60 measures the current resonant frequency of the piezoelectric beam 59. The controller 132 controls the drive/detection device 60, and receives its detected frequency data so that the controller 132 can determine if the resonant frequency has changed, which could indicate adsorption of the target gas onto the metal coating 62.

In one example, the cantilevered detector 58 provides redundancy and acts as an additional fail-safe mechanism for the SPR system 10. The cantilevered detector 58 bases its detection on adsorption of a sample gas (e.g., which may contain a target gas that is a contaminant such as $H_2S$ gas) by the metallic coating 62. The cantilevered beam 59 is, in one example, composed of a piezo-electric material, such as quartz or lead zirconate titanate ("PZT"). Adsorption of the target gas by the metallic coating 62 modifies the beam's mass and shifts its resonant frequency, which is detected by controller 132 monitoring a piezoelectric signal response from the beam 59. The cantilever measurement is used to either confirm the presence of the target gas or to enable an alarm state in the event of SPR system 10 failure (e.g., to indicate that a previous level of sensor redundancy is no longer available). After each measurement, the metallic coating 62 is heated to clean and/or release adsorbed material from the metallic coating 62 for continuous operation. The addition of the cantilever detection mechanism provides a fail-safe redundant device with minimal cross-sensitivity.

Although only one cantilevered detector 58 is shown in FIG. 5, it is understood that a plurality of them could be utilized in a configuration similar to FIG. 1 in which one cantilevered detector 58 is exposed to the sample gas 20A, and one cantilevered detector 58 is exposed to the reference gas 20B. The cantilevered detector 58 exposed to the reference gas 20B could provide a baseline for comparison against the cantilevered detector 58 exposed to the sample gas 20A. This would allow rejection of ambient vibrations and could provide for enhanced sensitivity.

Figure 6:
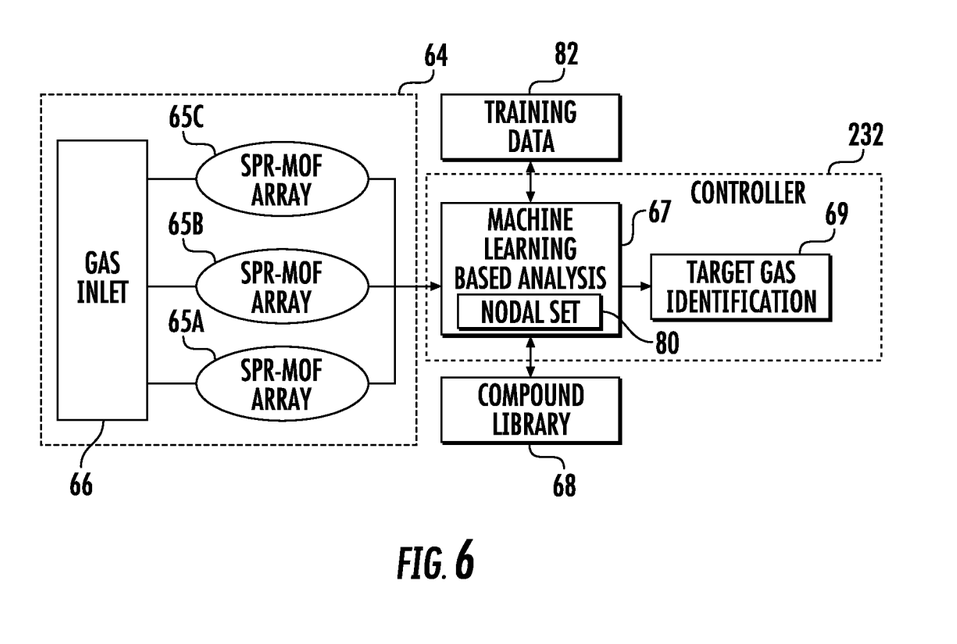
FIG. 6 schematically illustrates an example chip that includes an array of SPR detectors.

FIG. 6 schematically illustrates a microphotonic chip 64 (e.g., a silicon chip) that includes a plurality of arrays 65 of SPR metal oxide frameworks (MOFs) in an "on-chip" design. Each array 65 includes a plurality of SPR detectors 11, each utilizing a MOF as its metal layer 16. A plurality of different MOFs are used which have differing porosities and differing binding affinities for a plurality of different target gases. A gas inlet 66 provides a sample gas to the plurality of SPR-MOF arrays 65, which determine reflection and electrical properties of the sample gas. In one example, the gas inlet 66 includes a fluidic switch that controls a flow of gas to the arrays 65.

The controller 232 receives a set of historical training data 82 that has been gathered by the SPR-MOF arrays 65 when exposed to a plurality of different training gases having known compositions in a compound library 68. The training data includes electrical and/or optical characteristics observed from the SPR-MOF arrays 65 (or from a different, but substantially similar configuration of SPR-MOF arrays) when exposed to the chemical compounds from the library 68. The controller 232 performs a machine learning technique to generate a nodal set 80 that represents correlations in the set of historical training data 82. In one example, the nodal set 80 includes a deep neural network, such as a convolutional neural network (CNN), a recurrent neural network (RNN), or a combined RNN-CNN in which the RNN provides a wrapper around the CNN. A CNN captures spatial correlations, and an RNN captures temporal correlations. The combined RNN-CNN captures both spatial and temporal information of the target gas. In another example, other statistical machine learning approaches like random forests, XGBoost, Support Vector Machines, decision trees, and Monte Carlo methods to name a few, can also be used to capture these correlations.

A machine learning-based analysis (schematically shown as 67) is performed by controller 232 on the determined properties from the SPR-MOF arrays 65. The analysis 67 utilizes the nodal set 80 that was previously trained with historical training of the training gases. The machine learning-based analysis 67 provides an identification 69 of whether any of those target gases are present in the sample gas 20.

Figure 7A:
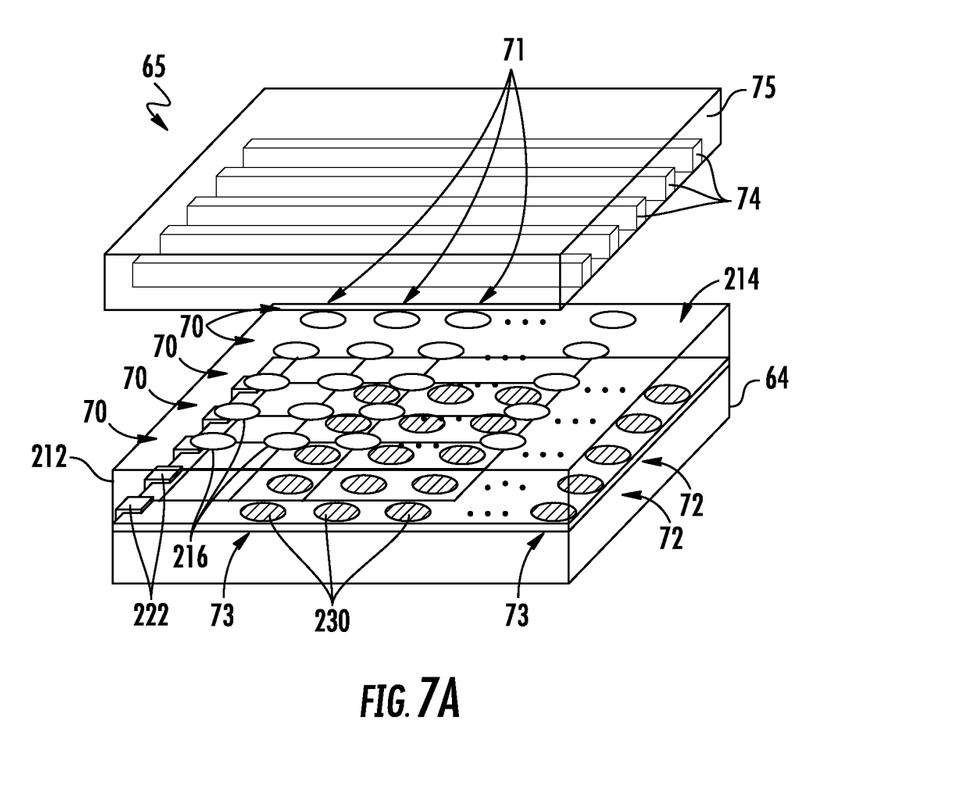
FIG. 7A schematically illustrates a partially exploded perspective view of an example SPR array.

FIG. 7A schematically illustrates a partially exploded perspective view of an example SPR-MOF array 65. The SPR-MOF array 65 includes a plurality of discrete MOFs 216 that are anodically bonded onto a surface 214 of a glass block 212. Each MOF 216 has an associated photodetector 230 configured to measure a reflection property of reflections of a beam from an interface of its associated MOF 216 and the surface 214. The photodetectors 230 and glass block 212 are situated on top of silicon chip 64, which acts as a substrate.

The photodetectors 230 can use a refractive index of beams reflected from the interface of a MOFs 216 and surface 214 as a measure of the MOF's sensitivity to the density/mass of the target gases it is exposed to.

In the SPR-MOF array 65, the MOFs 216 are arranged into a plurality of MOF rows 70 and a plurality of MOF columns 71 arranged in an M×N array. The photodetectors 230 are similarly arranged into a plurality of photodetector rows 72 and a plurality of photodetector columns 73 in an M×N array. In one non-limiting example, there are five rows (M=5) and ten columns (N=10) in each array. The MOF columns 71 and photodetector columns 73 are offset from each other to accommodate a distance traveled by reflected beams that reflect from the interface of the MOFs 216 and the surface 214 towards the photodetectors 230.

A channeling layer 75, shown as separate from the glass block 212 for illustrative purposes in FIG. 7A, abuts the surface 214 of the glass block 212. The channeling layer 75 includes a plurality of fluidic microchannels 74, one for each row 70. Each fluid microchannel 74 corresponds to one of the rows 70 of MOFs 216 and delivers the sample gas to the MOFs 216 in its corresponding row 70. In one example the channeling layer 75 is at least partially composed of quartz or silica.

A plurality of lasers 222, each corresponding to a single MOF row 70 and a single photodetector row 72, emit light that is delivered at predefined angles to each of the MOFs 216 in its row through the glass block 212. In one non-limiting example the laser 222 is a diode laser. The output wavelength of the diode laser can be selected to have an output wavelength in the range of 400 nm to 12,000 nm in one example, in another example the output wavelength range can be from 500 nm to 800 nm. The wavelength selection is related to the interaction of the light with the metal surface to establish the surface plasmon resonance or the absorption coefficient of the material near the metal layer, such as a resonant vibrational mode of the MOF or target gas.

In one example, different types of lasers 222 are used for different photodetectors of the photodetector rows 72, because some lasers may provide better resonance than others for certain target gases. As an example, methane has a vibrational mode around 3,300 nm. The laser 222 and detector in a photodetector row 72 could be optimized to detect for methane by emitting and receiving 3,300 nm light. In another example, $H_2S$ binds to gold. A surface plasmon resonance could can be established with 658 nm laser light. The laser 222 and photodetectors at a photodetector row 72 could be sensitive to changes in light of wavelength 658 nm enabling the detection in a change in the reflectivity of the metal layer.

The glass block 212 provides a plurality of three-dimensional waveguides in a tree topology that branch the light from the lasers 222 to the MOFs 216 at predefined angles. In one example, an ultrafast laser inscription (ULI) method is used to define the three-dimensional waveguide light propagation paths within the glass block 212. In one example, each 3D waveguide propagates light from a single laser 222 to a corresponding single MOF row 70 that is reflected down to a single photodetector row 72.

Figure 7B:
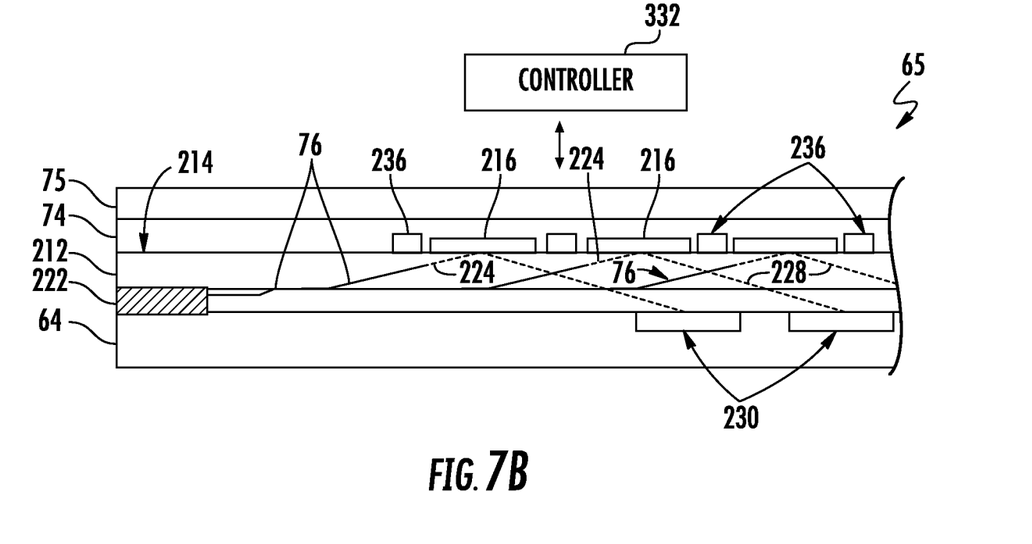
FIG. 7B schematically illustrates a side view of the SPR array of FIG. 7A.

FIG. 7B schematically illustrates a side view of a SPR-MOF array 65 that depicts the 3D waveguide 76 for a given MOF row 70 (shown in FIG. 7A), depicts the beams 224 that are emitted from a laser 222 and are propagated by the waveguide 76, and depicts the reflected beams 228 that reflect from the interface of the MOFs 216 and the surface 214. The 3D waveguide 76 for each MOF row 70 is configured to provide individual beams 224 from the laser 222 to individual ones of the MOFs 216 in its given MOF row 70.

As shown in FIG. 7B, a plurality of heaters 236 are disposed between the MOFs 216. The heaters 236 are configured to induce desorption of analytes from the MOFs 216 through heating.

Controller 332 is operable to control the lasers 222 to pulse the beams 224 to the MOFs 216, to control the photodetectors 230 that receive the reflected beam 228, and to control the heaters 236 to induce desorption. The controller 332 is also operatively connected to the MOFs 216 for determining an electrical property of the MOFs 216 during SPR, and to the photodetectors 230 for measuring a reflection property of the reflections of the respective beams off of the metal surfaces. In one example, each photodetector has a diameter on the order of 80 microns.

Figure 8:
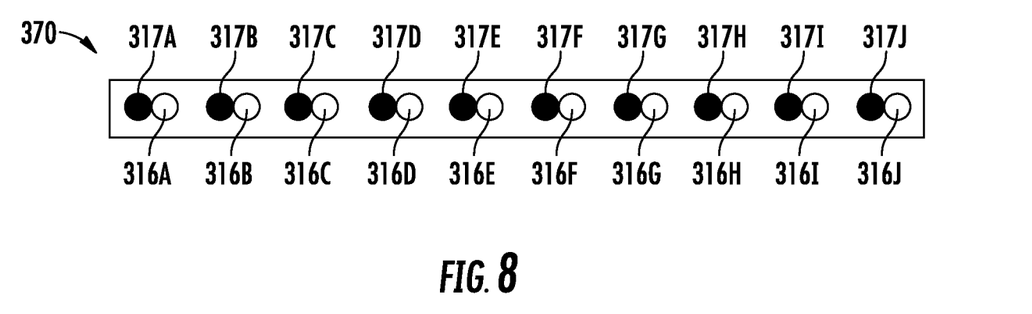
FIG. 8 schematically illustrates a row of an example SPR array.

FIG. 8 schematically illustrates an example row 370 of MOFs 316A-J each of which has an adjacent companion MOF 317A-J that has the same composition. Each companion MOF 317 is coated to prevent adsorption of analytes to the companion MOF 317. In the example of FIG. 8, the controller 332 is configured to compare each individual electrical property and/or the reflection property from the plurality of MOFs 316 (where adsorption of analytes can occur) to the electrical property and/or reflection property of the companion MOFs 317 (where adsorption cannot occur) in determining whether the sample gas includes one of the plurality of target gases. In this sense, the companion MOFs 317 serve as a baseline, and a similar response from one MOF and its companion would indicate that the given target analyte is not present. In one example, the MOFs 316 and their companion metal layers 317 for a given array 65 are coplanar in a plane defined by the surface 214.

One approach to identifying a target gas is the so-called "dictionary approach" in which each target gas has a pre-defined signature, and the properties measured from a sample gas are compared against those signatures to determine if any predefined target gases are present. However, in many testing environments there is a high likelihood that the target gas will not be present on its own, but will rather be present with a variety of nuisance gases that may reduce the accuracy of the "dictionary approach."

Figure 9:
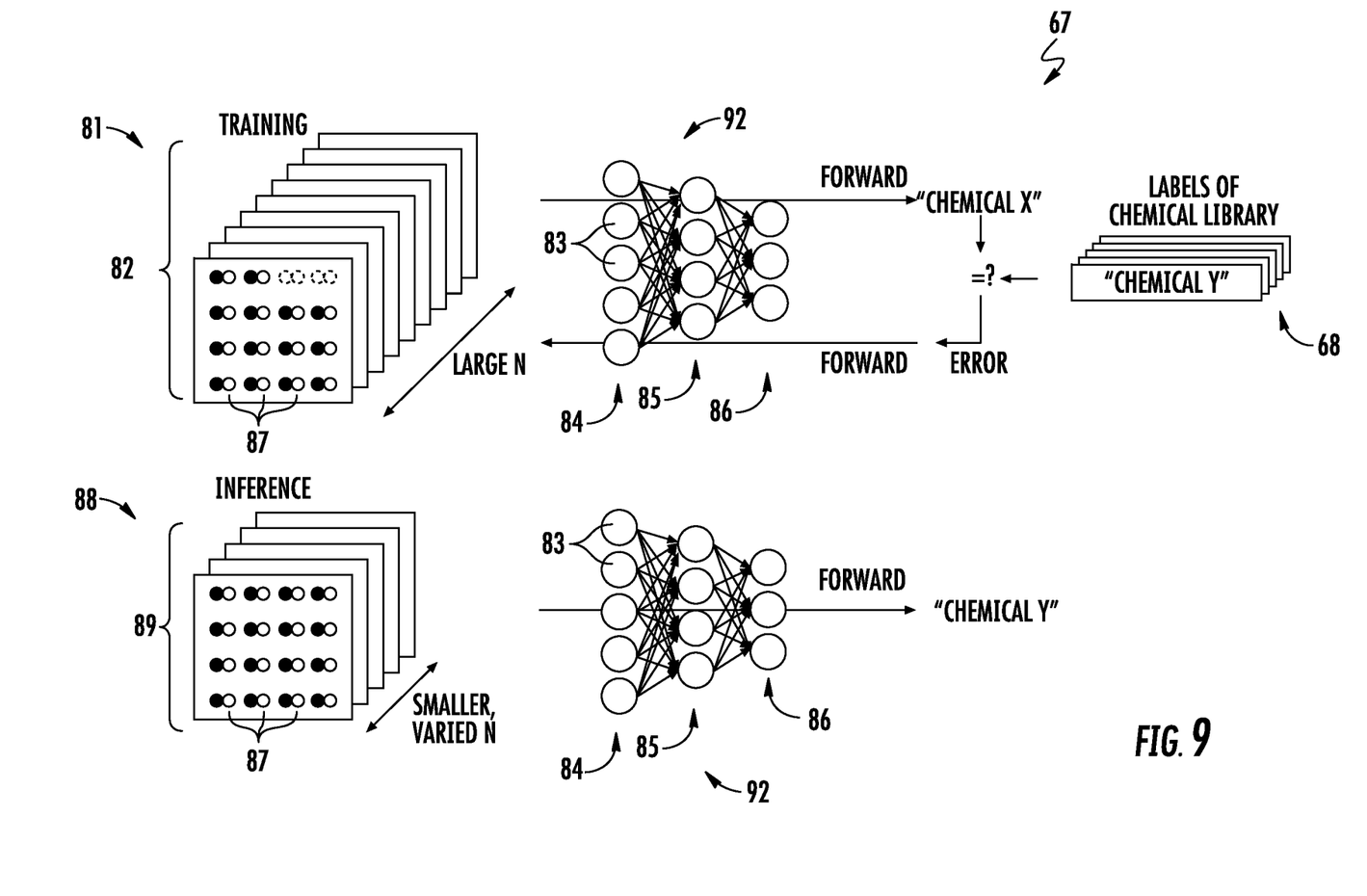
FIG. 9 schematically illustrates an example deep neural net analysis process for identifying a target gas.

Referring now to FIG. 9 with continued reference to FIG. 6, FIG. 9 schematically illustrates an example of the machine learning-based analysis 67 that improves upon the dictionary approach by utilizing a nodal set 80, which in the example of FIG. 9 is a neural network 92, that is trained from a large library of compounds (e.g., compound library 68 of FIG. 6). In one example, some of the training data 82 is gathered from target gases mixed with nuisance gases, so that the target gases can be detected in small concentrations amidst the nuisance gases. The controller 232 is configured to perform the machine learning-based analysis 67, and can store the neural network 92 in its memory.

FIG. 9 schematically shows how a smaller data set can be used for inferences ("smaller, varied N" in FIG. 9) than the data set used for training ("large N" in FIG. 9). That is because a RNN can suggest the most relevant regions, and the entire data set N does not have to be given to the CNN to make a decision about the gas that a sensor was exposed to.

During a training phase 81, the neural network 92 is trained from a large set of training data (schematically shown as 82) as gathered by a plurality of sensors 87 exposed to a plurality of target gases from the chemical library 68.

The training data includes electrical and/or optical characteristics observed from the sensors 87 when exposed to the chemical compounds from the library 68. The sensors 87 could include any of the SPR detectors 11 discussed herein, for example, including the array-based sensors of FIGS. 7A, 7B, and 8. The observed characteristics could include electrical properties during SPR of a metal layer 16, such as changes of resistance of a metal layer during SPR, amplitude of an electrical signal provided across the metal layer 16 during SPR, a frequency of an electrical signal provided across the metal layer 16 during SPR, a dielectric constant, a dielectric strength, electrical resistivity and conductivity, permittivity, breakdown field, mobility electrons, diffusion coefficient electrons, diffusion coefficient holes, and electron thermal velocity, for example. The observed characteristics could also include optical properties such as an angle of minimum reflected intensity, absorbance, refractive index, transmittance, dielectric constant, refractive index, radiative recombination coefficient, optical photon energy, and adsorption coefficient, for example.

Another type of detector that could be used to obtain training data includes photoacoustic detectors. Generally speaking, photoacoustic detectors rely on interaction between light and a target substance to produce an acoustic response that can be measured and used for detection. A photoacoustic detector may include a chamber, a pulsed light of a pre-selected frequency, and a microphone. Ambient air is circulated through the chamber. The light is pulsed through the chamber and the microphone listens for an acoustic response. The pre-selected frequency coincides with an absorption frequency of the target substance. If the target substance is present in the air, the substance absorbs a portion of the light during light pulses. As the substance absorbs light it heats and causes a local pressure increase in the air. Between pulses the substance cools, thereby producing a local pressure decrease in the air. The alternating pressure increases and decreases manifest as an acoustic signal that can be heard by the microphone and used to identify that the substance is present in the air.

The neural network 80 is trained 81 by associating its observations from a given target gas with the identity of the target gas from the library 68. Instead of simply relying on the dictionary approach which dictates what the predefined signature is for a given compounds, the neural network 80 learns its own signatures based on the training data 82.

The example simplified neural network 80 shown in FIG. 9 includes a plurality of nodes 83 arranged into an input stage 84 (first column), a plurality of hidden intermediate stages (middle columns 85, one of which is illustratively shown in FIG. 9), and an output stage 86 (third column) The arrows between nodes 83 in subsequent stages represent discrete weight values that represent the strength of a correlation between two nodes 83, which is indicative of how strong an inference can be drawn between the two nodes 83.

In an inference stage 88, the neural network 80, having been trained on the training data 82 for a gas sample, is presented with a smaller set of input data 89 which also comes from sensors 87. The input data 89 is analyzed using the neural network 80 to identify a "chemical Y" corresponding to what the neural network 80 believes to be chemicals present in the gas sample.

Deep learning algorithms benefit from large amounts of labelled training data to generate a robust mathematical model that can be used for inference on testing data. Recurrent Neural Networks (RNN) are optimal for exploiting the temporal characteristics of either absorption or desorption characteristics of the sensing element for discriminating the chemical compound species. Spatial correlations can be exploited using Deep Convolutional Neural Networks (DCNN), especially when the sensing elements are laid out in a M×N array. The snapshots of the M×N array are taken at specific time intervals corresponding to electrical properties, such as amplitude changes or frequency changes, influencing chemical gas adsorption or desorption.

The example neural network 80 fuses both RNN and CNN, yielding a method that can exploit both the temporal and spatial characteristics in parallel aiding the identification of a given chemical compound with reduced latency and low power consumption. In one example, the RNN provides a wrapper on top of the CNN.

At time t, nodes 83 with recurrent edges receive two inputs, where $x\hat{}((t))$ is the current data and $h\hat{}((t-1))$ is the network's previous state. The output $y'\hat{}((t))$ is calculated from the hidden node $h\hat{}((t))$ at time t. In one example, the following calculations are required at each time step, $$h\hat{}((t)) = \sigma(W\hat{}hx\ x\hat{}((t)) + W\hat{}hh\ h\hat{}((t-1)) + b\_h)$$

$$y'\hat{}((t)) = \text{softmax}(W\hat{}yh\ h\hat{}((t)) + b\_y)$$

where: $W\hat{}hx$ represents the matrix of weights between the input 84 and hidden layer 85;

$W\hat{}hh$ represents the matrix of weights between the hidden layer 85 and itself at adjacent time steps; and $W\hat{}yh$ represents the matrix of weights between the output 86 and the hidden layer 85.

The bias parameters b_h and b_y allows each node 83 to learn an offset. The conventional method of using a dictionary approach and ranking the results may increase in latency and computational resources, whereas the approach described above can avoid such issues.

The trained model produced by the RNN and CNN on the sequence of different chemical wavelengths can predict different correlation scores corresponding to the presence of the explosives. This inference step evolves over time and reduces the latency considerably, as only a very small sample time is required to accurately predict the presence of hazardous gases.

Although example embodiments have been disclosed, a worker of ordinary skill in this art would recognize that certain modifications would come within the scope of this disclosure. For that reason, the following claims should be studied to determine the scope and content of this disclosure.

What is claimed is:

1. A surface plasmon resonance (SPR) detection system, comprising:
    a light propagation structure comprising a surface and a plurality of waveguides;
    a plurality of metal layers comprising different metal oxide frameworks (MOFs) that are spaced apart from each other and have differing porosities and different binding affinities for a plurality of different target gases, the plurality of metal layers arranged in an array on the surface and exposed to a sample gas;
    a plurality of light sources configured to provide respective beams through the plurality of waveguides to the surface that cause SPR of each metal layer;
    an array of photodetectors, each associated with one of the metal layers, and configured to measure a reflection property of a reflection of one of the beams from an interface of the surface and its associated metal layer; and
    a controller configured to determine an electrical property of the plurality of metal layers during the SPR, and determine whether any of the target gases are present in the sample gas based on at least one of the electrical properties and the reflection properties of the metal layers.

2. The SPR detection system of claim 1, wherein:
    each metal layer is adjacent to a companion metal layer that is coated to prevent adsorption of analytes to the companion metal layer; and
    the controller is configured to compare at least one of the electrical property and the reflection property from each of the plurality of metal layers to at least one of an electrical property and a reflection property from its corresponding companion metal layer as part of the determination of whether any of the target gases are present in the sample gas.

3. The SPR detection system of claim 2, wherein each metal layer has the same MOF composition as its companion metal layer.

4. The SPR detection system of claim 2, wherein the plurality of metal layers and companion metal layers are coplanar.

5. The SPR detection system of claim 1, wherein:
    the plurality of light sources comprises a respective light emitter for each row of the array of metal layers; and
    wherein each waveguide is configured to guide a beam from a given one of the light emitters towards the metal layers of its associated row at predefined angles.

6. The SPR detection system of claim 1, comprising:
    a plurality of heaters disposed adjacent to individual ones of the metal layers, each configured to induce desorption of analytes from its adjacent metal layer by heating its adjacent metal layer.

7. A chemical detection system, comprising:
    a plurality of detectors arranged for collecting data from a gas sample, each detector comprising a respective metal layer, wherein each of the metal layers includes a different metal oxide framework (MOF), the metal layers are spaced apart from each other and have differing porosities, and various ones of the metal layers having differing binding affinities for a plurality of target gases, the plurality of detectors configured to use at least one of surface plasmon resonance (SPR) and photoacoustic detection techniques to collect data about the gas sample; and
    a processor configured to perform a machine learning-based analysis to determine whether any of the target gases are present in the gas sample based on the data collected by the plurality of detectors from the gas sample.

8. The chemical detection system of claim 7, wherein to perform the machine learning-based analysis, the processor is configured to:
    apply at least one machine learning technique to a set of historical training data to produce a nodal set that represents at least one of spatial and temporal correlations in the set of historical training data, the training data gathered by the plurality of detectors when exposed to a plurality of different training gases having known compositions; and utilize the nodal set to determine whether any of the target gases are present in the gas sample based on the data collected by the plurality of detectors from the gas sample.

9. The chemical detector system of claim 8, wherein the nodal set comprises a neural network comprising at least one of a recurrent neural network and a convolutional neural network.

10. The chemical detector system of claim 7, wherein the data collected by the plurality of detectors from the gas sample includes a change in resistance across a plurality of the metal layers when the plurality of metal layers are resonating and are exposed to the gas sample.

11. The chemical detector system of claim 7, wherein the data collected by the plurality of detectors from the gas sample includes a change in amplitude, frequency, or both, of respective electrical signals across respective ones of the metal layers when the respective ones of the metal layers are resonating and are exposed to the gas sample.

12. The chemical detector system of claim 7, wherein the data collected by the plurality of detectors from the gas sample includes changes in reflection properties of beams reflected from the metal layers when the metal layers are resonating and are exposed to the gas sample.

13. The chemical detector system of claim 7, wherein the data collected by the plurality of detectors from the gas sample includes desorption data indicative of a time needed for analytes from the gas sample to desorb from various ones of the metal layers.

14. The SPR detection system of claim 1, wherein:
the plurality of metal layers includes a plurality of rows and a plurality of columns of metal layers; and
the array of photodetectors includes a plurality of rows and a plurality of columns of photodetectors.

15. The SPR detection system of claim 1, wherein:
the array of photodetectors includes a plurality of rows of photodetectors;
the array of metal layers includes a plurality of rows of metal layers; and
each waveguide is configured to propagate light from a single one of the plurality of light sources to a corresponding single one of the rows of photodetectors.

16. The chemical detector system of claim 7, wherein:
the plurality of metal layers includes a plurality of rows and a plurality of columns of metal layers; and
the array of photodetectors includes a plurality of rows and a plurality of columns of photodetectors.

17. The chemical detector system of claim 7, wherein:
the array of photodetectors includes a plurality of rows of photodetectors;
the array of metal layers includes a plurality of rows of metal layers; and
each waveguide is configured to propagate light from a single one of the plurality of light sources to a corresponding single one of the rows of photodetectors.

* * * * *

UNITED STATES PATENT AND TRADEMARK OFFICE
CERTIFICATE OF CORRECTION

| | |
|---|---|
| PATENT NO. | : 11,988,602 B2 |
| APPLICATION NO. | : 17/054300 |
| DATED | : May 21, 2024 |
| INVENTOR(S) | : Lincoln et al. |

It is certified that error appears in the above-identified patent and that said Letters Patent is hereby corrected as shown below:

In the Claims

Claim 16, Column 16, Line 20, "the array of photodetectors" should read --the plurality of detectors--

Claim 17, Column 16, Line 23, "the array of photodetectors" should read --the plurality of detectors--

Claim 17, Column 16, Line 25, "the array of metal layers" should read --the metal layers--

Claim 17, Column 16, Line 28, "the plurality of light sources" should read --a plurality of light sources--

Signed and Sealed this
Third Day of September, 2024

Katherine Kelly Vidal
*Director of the United States Patent and Trademark Office*